United States Patent
Graser et al.

(10) Patent No.: US 6,805,830 B1
(45) Date of Patent: Oct. 19, 2004

(54) METHOD FOR PRODUCING A SENSOR ELEMENT

(75) Inventors: Theodor Graser, Stuttgart (DE); Olaf Jach, Böblingen (DE); Hans-Jörg Renz, Leinfelden-Echterdingen (DE); Harald Neumann, Vaihingen (DE); Anton Hans, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/194,773

(22) PCT Filed: Feb. 21, 1998

(86) PCT No.: PCT/DE98/00525

§ 371 (c)(1),
(2), (4) Date: Mar. 31, 1999

(87) PCT Pub. No.: WO98/45695

PCT Pub. Date: Oct. 15, 1998

(30) Foreign Application Priority Data

Apr. 4, 1997 (DE) .......................................... 197 13 904

(51) Int. Cl.$^7$ ................................................ H05B 6/00
(52) U.S. Cl. ....................................... 264/430; 264/678
(58) Field of Search ................................ 264/430, 678

(56) References Cited

U.S. PATENT DOCUMENTS

| 4,403,207 A |   | 9/1983  | Murphy et al. ................ 338/34 |
| 5,144,249 A |   | 9/1992  | Kurishita et al. ............ 324/439 |
| 5,573,650 A |   | 11/1996 | Fukaya et al. .............. 204/424 |
| 5,871,313 A | * | 2/1999  | Nenadic et al. ............. 409/138 |

\* cited by examiner

Primary Examiner—Christopher A. Fiorilla
(74) Attorney, Agent, or Firm—Kenyon & Kenyon

(57) ABSTRACT

A method for manufacturing a sensing element is provided, in particular for determining the oxygen content in exhaust gases of internal combustion engines, a composite construction having at least one ceramic paste (green film) present in film form being sintered to yield the sensing element, and sharp edges of the sensing element being blunted before sintering to increase the thermal shock resistance of the sensing element.

9 Claims, 2 Drawing Sheets

METHOD FOR PRODUCING A SENSOR ELEMENT

This application is a 371 of PCT/DE98/00525 filed Feb. 21, 1998.

FIELD OF THE INVENTION

The present invention relates to a method for manufacturing a sensing element, in particular for determining the oxygen content in exhaust gases of internal combustion engines.

BACKGROUND INFORMATION

Sensing elements are configured, for example, as so-called planar sensing elements, which comprise a composite construction of individual layers arranged one above another in film form. The individual films of this composite construction are arranged one above another in defined fashion, resulting in various functional layers. The individual films of the composite construction are, for example, laid onto one another by means of a screen printing technique, as green films. The sensing elements usually have solid electrolyte films, electrode films, heating, conductor films, insulation films, and protective films. Conventional sensing films may also have substrate films with printed electrolyte layers, aluminum oxide substrate films with semiconductor sensors ($TiO_2$, $SrTiO_3$). Instead of laying the green films onto one another, the latter, may also be obtained by individual printing steps. The arrangement of these different films one above another results in a laminated composite construction from which the sensing element is obtained by sintering.

During testing of the sintered sensing element, or during utilization thereof as intended, the individual layers of the sensing element are exposed to different temperatures. Because of these sudden temperature changes which occur with differing intensity, the sensing elements experience a temperature shock which leads to the occurrence of mechanical stresses in the surface region, in particular at the edges of the sensing element. In order to increase the temperature shock resistance of the sensing elements, U.S. Pat. No. 5,144,249 describes blunting the edges of the sensing element, i.e. equipping them with a chamfer. Chamfering is accomplished by way of a grinding operation sintering and after sectioning of the sensing elements. It is disadvantageous to subject completed sensing elements to a mechanical machining operation which is relatively complex and may lead to undesired damage to the sensing elements.

SUMMARY OF THE INVENTION

The method according to the present invention offers, in contrast, the advantage that blunting of the edges of the sensing element may be accomplished in a simple manner without the risk of impairing the sensing element. The edges of the sensing element are blunted prior to sintering, as a result, is possible to blunt the edge in any desired geometry using simple, non-chip-removing methods. In particular, blunting of the edges may be accomplished in a form deviating from a flat surface, for example in a convex or concave form, so that mechanical stresses which occur as a consequence of a temperature shock to the blunted edges cannot result in the creation of cracks.

In a preferred embodiment of the present invention, provision is made for the edges to be blunted by shaping, preferably by stamping of the film composite construction present in the green state. It is thereby possible, using a simple stamping tool, to shape the edges of the composite construction of green films in simple fashion, due to their soft consistency prior to sintering. By configuring a corresponding stamping tool, a blunting of the edges may be executed in any desired form. It is particularly advantageous if, once the stamping tools have been used, the stamping films laid in place are ones which allow shaping only of the edge region of the sensing element, and leave the other regions, in particular the planar regions of the sensing element, unmodified. In order to prevent adhesion of the green film composite construction of the sensing element in the stamping tool, the stamping film may be advantageously equipped with an anti-adhesion coating, in particular Teflon.

In a preferred embodiment, blunting of the edges is accomplished by use of a laser treatment. Use of the laser treatment makes it possible to advantageously accomplish noncontact blunting of the edges of the sensing element in the green state, so that any mechanical loads on the green film composite construction may be ruled out. It is possible to advantageously adjust the contour of the blunted edges of the sensing element by using a mask of an excimer laser.

By using the laser treatment, blunting of the edges may preferably be accomplished even before sectioning of the green films present in the composite construction, so that blunting of the edges may be accomplished very effectively. At the same time, the break points of the wafer, with the individual sensing elements may thereby be defined.

It is also preferred, in particular, if the laser treatment simultaneously accomplishes blunting of the edges and sectioning of the green film composite construction. By adjusting the laser output and the geometry of the laser beam, it is thus possible to accomplish edge blunting and sectioning in one operation.

DETAILED DESCRIPTION

Figure 1:
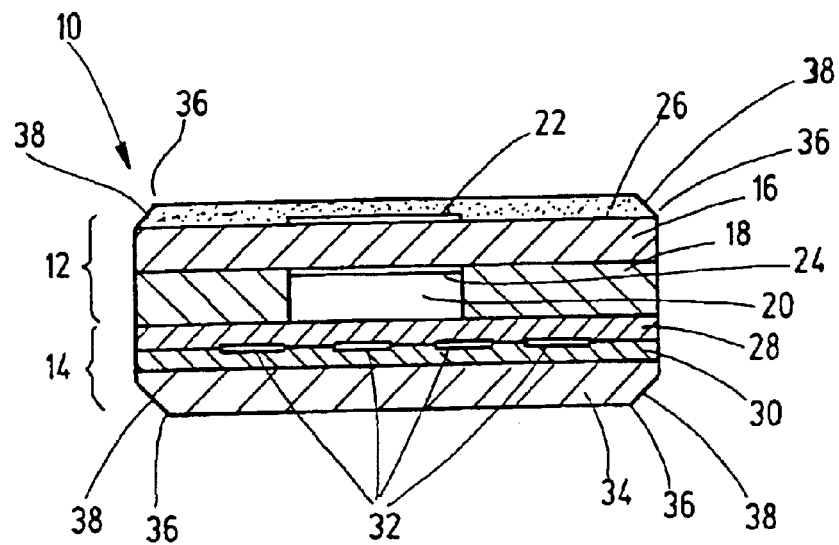
FIG. 1 shows a sectioned depiction through a sensing element.

FIG. 1 shows a sectioned depiction through a sensing element 10 which may serve, for example, to determine an oxygen content in exhaust gases of internal combustion engines in motor vehicles or of furnaces. Since the configuration and function of a sensing element 10 of this kind are commonly known, only the configuration that is important for explaining the present invention will be described below. The sensing element substantially has an elongated, flat-plate configuration that is composed of individual strata of various functional layers. As FIG. 1 illustrates, sensing element 10 possesses an electrochemical measurement cell 12 and a heating element 14. Measurement cell 12 includes a first solid electrolyte film 16 and a second solid electrolyte film 18 which has an integrated reference gas conduit 20. A measurement electrode 22 is associated with a measuredgas-side surface of electrolyte film 16, and a reference electrode 24 is associated with the surface associated with reference gas conduit 20. A porous cover layer 26 is arranged above measurement electrode 22.

Heating element 14 has heating conductors 32 embedded in insulation layers 28 and 30. Adjacent to insulation layer 30 is a further cover layer 34.

Solid electrolyte films 16 and 18 and cover layer 34 are made, for example, of a stabilized zirconium oxide ($ZrO_2$). Electrodes 22 and 24 and heating conductors 32 are made, for example, of a platinum cermet. Insulation layers 28 and 30 are made, for example, of a mixture of aluminum oxide ($Al_2O_3$) and glass-forming components.

The entire composite construction of individual layers possesses, when viewed in cross section, an approximately parallelepipedal configuration, at least edges 36 running in the longitudinal direction of the sensing element have a chamfer 38.

Sensing element 10 is manufactured by successive lamination of the individual layers onto cover layer 34, which at the same time constitutes a support. Definition of the layers may be accomplished by screen printing of a paste material which has the respective composition of the layer. After completion of this lamination, there results a composite construction of so-called green films of the individual layers, which possess a relatively soft consistency. The composite construction is a then subjected in a conventional manner to a sintering operation, sensing element 10 is created under the action of temperature and optional pressure.

According to the present invention, provision is now made, before sintering, for patterning chamfers 38 of edges 36. Individual possibilities for achieving chamfers 38 will be discussed below.

Figure 2:
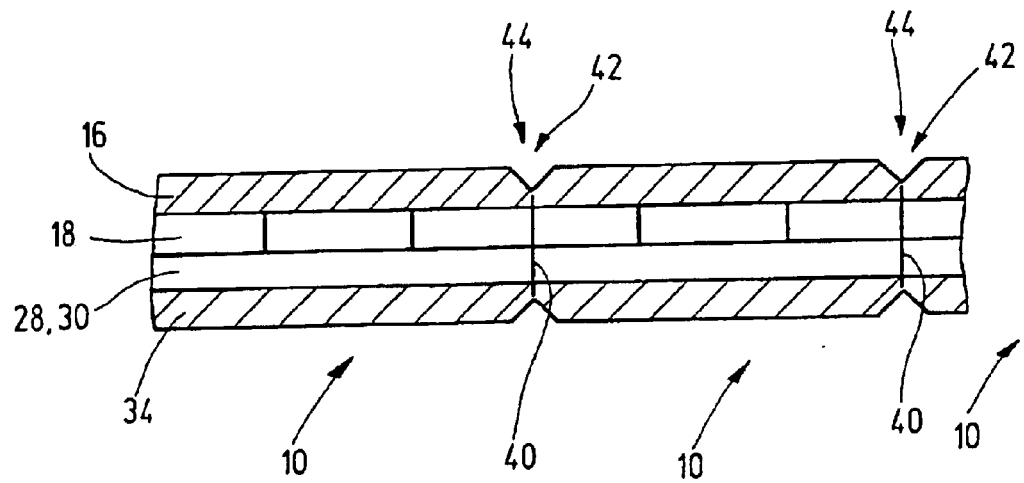
FIG. 2 shows a sectioned depiction through a panel of several sensing elements.
Figure 3:
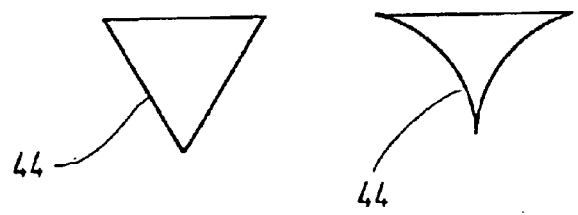
FIG. 3 shows geometrical structures of lasers.

FIG. 2 shows a portion of a panel of a plurality of sensing elements 10 present in the green state. In this, the individual layers of sensing elements 10 are laminated simultaneously for a plurality of sensing elements 10, and the composite construction of green films for one sensing element 10 is then sectioned out. FIG. 2 shows portions of three sensing elements 10. Parts identical to those in FIG. 1 are given identical reference characters, and will not be explained again. After lamination, cutting lines 40 are defined at which sectioning of sensing elements 10 is accomplished. Prior to sectioning of sensing elements 10, a defined surface depression 42 may be introduced at cutting lines 40. This surface depression 42 may be executed, for example, using an excimer laser 44 which has a specific mask. FIG. 3 shows, for example, two possible masks. According to the left-hand depiction, excimer laser 44 may possess a triangular mask so that surface depressions 42 are triangular in accordance with this depression. According to the exemplary embodiment depicted on the right in FIG. 3, the mask may also have delimiting surfaces extending in concave fashion. Other exemplary embodiments which exhibit mixed forms of planes running at various angles and/or concave and/or convex delimiting surfaces are also possible.

Figure 4:
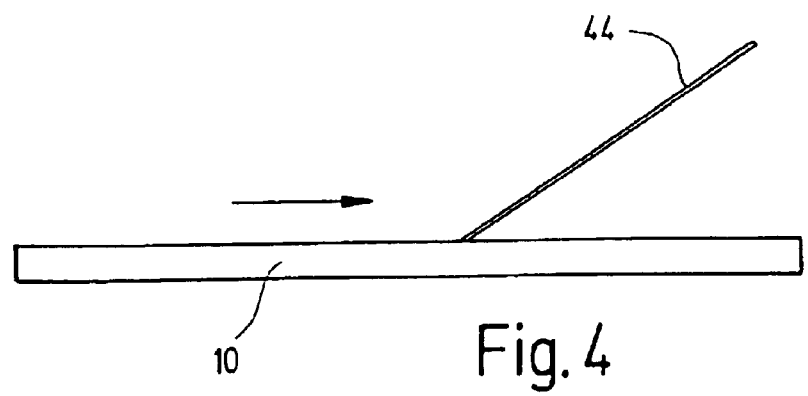
FIG. 4 shows a use of a laser according to the present invention.

As FIG. 4 illustrates, excimer laser 44 is moved along the surface of the composite construction of green films. For this purpose, either excimer laser 44 may be movable, and/or the green films may be moved past excimer laser 44. Surface depression 42 is patterned in terms of its depth and feed rate in accordance with the output setting of excimer laser 44.

The patterning of surface depressions 42 yields blunted edges 36 with their chamfers 38. Sensing elements 10 are then sectioned along cutting lines 40, and are then subjected to the sintering operation. Sensing element 10 shown in cross section in FIG. 1 is then created. Because chamfers 38 are patterned while the films of sensing element 10 are in the green state, and because of the noncontact patterning with excimer laser 44, sensing element 10 is not subjected to any mechanical stress, thus substantially ruling out damage.

Sectioning of the sensing elements may be accomplished via a further treatment with an excimer laser which has a corresponding mask. It is also possible, however, by selecting a mask and an output level for excimer laser 44, to execute the surface depression and sectioning in one operation.

Figure 5:
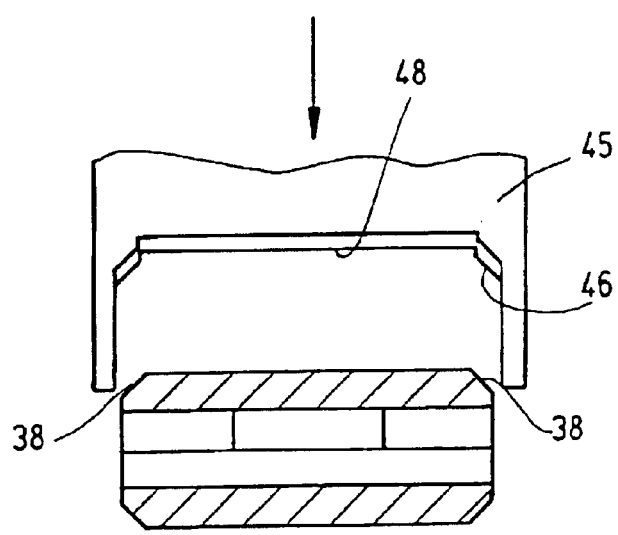
FIG. 5 shows a use of a stamping technique according to the present invention.

FIG. 5 indicates a further possibility for patterning chamfers 38. In this, a sensing element 10 is acted upon by a stamping apparatus 45 after sectioning of the composite construction of green films. Stamping apparatus 45 possesses a contour 46 which allows shaping of edges 36 in such a way that the edges 36 then exhibit chamfers 38. Depending on the shaping of contour 46, chamfer 38 may also have a different contour as a result of stamping, for example planar and/or convex and/or concave sections. Contour 46 of stamping apparatus 45 may be created either by manufacturing a corresponding stamping apparatus 45, or by laying a stamping film 48 into stamping apparatus 45. Stamping film 48 is preferably equipped with an anti-adhesion coating, for example Teflon or titanium nitride. Since the green films still have a relatively soft consistency in the case of this shaping as well, chamfers 38 may easily be stamped in without causing impairment to the prefabricated sensing element 10.

Figure 6:
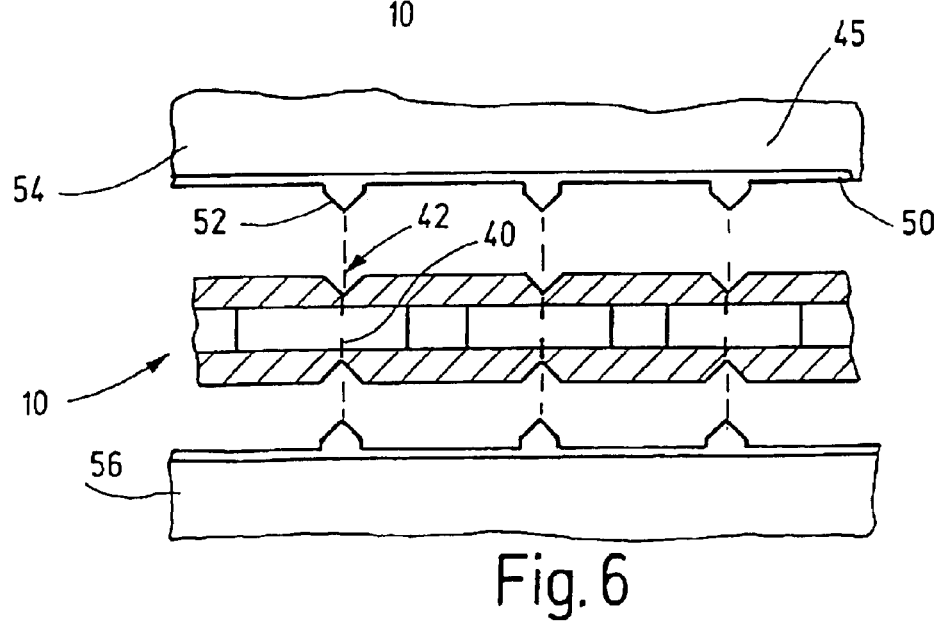
FIG. 6 shows a use of a stamping technique according to the present invention.

FIG. 6 shows a further exemplary embodiment in which stamping of a composite construction of sensing elements 10 may be accomplished. For this, stamping apparatus 45 possesses a stamping contour 50 which exhibits projections 52 corresponding to depressions 42. Stamping contour 50 may also be equipped with an anti-adhesion coating. With the exemplary embodiment shown in FIG. 6, it is easy to stamp a plurality of sensing elements 10 in a multiple panel with one stamping step, subsequent sectioning occurring along cutting lines 40.

Stamping apparatus 45 may advantageously have an upper die 54 and a lower die 56, so that the upper and lower sides of sensing elements 10 may be stamped simultaneously in one process step. Because of the relatively soft consistency of the as-yet unsintered sensing elements 10, surface depressions 42 may be stamped in with little energy expenditure, so that damage to the structure of sensing elements 10 may be excluded.

It is self-evident that when chamfers 38 are patterned either using excimer laser 44 or with stamping apparatus 45, both sides of sensing element 10 are processed. For this purpose, either an apparatus acting in double-sided fashion may be provided, or the green film composite construction of sensing elements 10 is turned over.

In sum, it is clear that the configuration of chamfers 38 in various contours, which is desirable in order to increase the temperature shock resistance of sensing element 10, may be effected using easily implemented actions. The outlay for tooling is relatively low, and the latter is subject essentially to no wear, so that long service lives may be expected. The additional use of consumable materials, for example as in the case of grinding of the sintered sensing element 10 defined in the existing art, is entirely eliminated.

What is claimed is:

1. A method for manufacturing a sensing element for determining oxygen content in exhaust gases of an internal combustion engine, comprising the steps of:

blunting edges of a composite arrangement for use as the sensing element to increase a thermal shock resistance of the sensing element; and sintering the composite arrangement to yield the sensing element, the composite arrangement including at least one ceramic paste present in film form;

wherein the step of blunting includes the step of blunting the edges of the composite arrangement by shaping, and the step of blunting the edges of the composite arrangement further includes the step of blunting the edges of the composite arrangement by stamping.

2. A method for manufacturing a sensing element for determining oxygen content in exhaust gases of an internal combustion engine, comprising the steps of:

blunting edges of a composite arrangement for use as the sensing element to increase a thermal shock resistance of the sensing element;

sintering the composite arrangement to yield the sensing element, the composite arrangement including at least one ceramic paste present in film form; and introducing a profile into a stamping apparatus for pre-pressing a laminate construction of unsintered films of the composites arrangement.

3. The method according to claim 2, further comprising the step of:

obtaining the profile by introducing a profiling film into the stamping apparatus.

4. The method according to claim 3, wherein the step of blunting further includes the step of obtaining the profile by introducing profiling film having an anti-adhesion coating into the stamping apparatus.

5. A method for manufacturing a sensing element for determining oxygen content in exhaust gases of an internal combustion engine, comprising the steps of:

blunting edges of a composite arrangement for use as the sensing element to increase a thermal shock resistance of the sensing element; and sintering the composite arrangement to yield the sensing element, the composite arrangement including at least one ceramic paste present in film form;

wherein the step of blunting the edges of the composite arrangement further includes the step of blunting the edges of the composite arrangement using a laser treatment.

6. A method for manufacturing a sensing element for determining oxygen content in exhaust gases of an internal combustion engine, comprising the steps of:

blunting edges of a composite arrangement for use as the sensing element to increase a thermal shock resistance of the sensing element; and sintering the composite arrangement to yield the sensing element, the composite arrangement including at least one ceramic paste present in film form;

wherein the step of blunting includes the step of blunting the edges of the composite arrangement using an excimer laser having definable masking.

7. A method for manufacturing a sensing element for determining oxygen content in exhaust gases of an internal combustion engine, comprising the steps of:

blunting edges of a composite arrangement for use as the sensing element to increase a thermal shock resistance of the sensing element; and sintering the composite arrangement to yield the sensing element, the composite arrangement including at least one ceramic paste present in film form;

wherein the step of blunting includes step of treating sectioned composite arrangements with a laser, the sectioned composite arrangements having a composition construction of green films.

8. The method according to claim 7, further comprising the step of:

sectioning the composite arrangement from a wafer, the wafer including the sectioned composite arrangements, wherein the treating step is performed prior to the sectioning step.

9. A method for manufacturing a sensing element for determining oxygen content in exhaust gases of an internal combustion engine, comprising the steps of:

blunting edges of a composite arrangement for use as the sensing element to increase a thermal shock resistance of the sensing element;

sintering the composite arrangement to yield the sensing element, the composite arrangement including at least one ceramic paste present in film form; and sectioning the composite arrangement from a wafer with a laser, the wafer including individual composite arrangements composed of a composite of green films, wherein the sectioning step is performed simultaneously with the blunting step, and wherein the blunting step includes the step of blunting the edges of the composite arrangement with the laser.

* * * * *